US00PP18815P3

(12) United States Plant Patent
Zaiger et al.

(10) Patent No.: US PP18,815 P3
(45) Date of Patent: May 13, 2008

(54) INTERSPECIFIC TREE NAMED 'BELLA CERISE'

(50) Latin Name: **Interspecific *Prunus* species**
Varietal Denomination: Bella Cerise

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 277 days.

(21) Appl. No.: 11/304,459

(22) Filed: Dec. 16, 2005

(65) Prior Publication Data

US 2007/0143883 P1 Jun. 21, 2007

(51) Int. Cl.
*A01H 5/00* (2006.01)

(52) U.S. Cl. ..... Plt./186

(58) Field of Classification Search ..... Plt./186
See application file for complete search history.

*Primary Examiner*—Anne Marie Grunberg
*Assistant Examiner*—Georgia Helmer

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Regular and productive bearer of medium to large size fruit.
2. Vigorous, semi-spreading tree growth.
3. Fruit with attractive red skin color.
4. Fruit with good flavor and eating quality.
5. Relatively uniform size and maturity of fruit throughout the tree.
6. Fruit with good storage and shelf life.

1 Drawing Sheet

Botanical description: Interspecific *Prunus* species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific and apricot trees, which are known to us, and mentioned herein, are 'Geo Pride' Interspecific (U.S. Plant Pat. No. 10,386), 'Flavor Queen' Interspecific (U.S. Plant Pat. No. 7,420) and the proprietary interspecific trees '38GH36', '352LC448' and '87EB101'.

ORIGIN OF THE VARIETY

The new and distinct variety of interspecific tree, maternal parent [(*Prunus salicina*×(*Prunus salicina*×*Prunus armeniaca*))×(*Prunus salicina*×(*Prunus salicina*×*Prunus armeniaca*))]×paternal parent [(*Prunus armeniaca*×(*Prunus salicina*×*Prunus armeniaca*))×(*Prunus salicina*×(*Prunus salicina*×*Prunus armeniaca*))], was originated by us in our experimental orchard located near Modesto, Calif. as a first generation cross between proprietary lines of immediate parents with field identification numbers '38GH36' and '352LC448'. The maternal parent (38GH36) originated from a cross between two interspecific parents, 'Geo Pride' (U.S. Plant Pat. No. 10,386) and 'Flavor Queen' (U.S. Plant Pat. No. 7,420). The paternal parent (352LC448) originated from a cross between a proprietary interspecific with field identification number (87EB101) and the interspecific 'Flavor Queen' (U.S. Plant Pat. No. 7,420). A large number of seedlings from these first generation cross were budded on older trees of 'Nemaguard' Rootstock (non-patented), to induce earlier fruit production, one such seedling exhibited desirable fruit characteristics and was selected in 1997 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree [(Plum×Plumcot)×(Plum×Plumcot)]×[(Apricot×Plumcot)×(Plum×Plumcot)] is of large size, vigorous, semi-spreading growth and a regular bearer of medium to large size fruit with good flavor and eating quality. The fruit is further characterized by having an attractive red skin color, firm flesh with a deep yellow color and being relatively uniform in maturity and size throughout the tree. In comparison to its maternal proprietary parent (38GH36), the skin of the new variety has pubescence compared to smooth slick skin and is approximately 18 days earlier in maturity. In comparison to its paternal proprietary parent (352LC448), the new variety has red skin color, compared to yellow and is approximately 5 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, 7 years of age, its flowers, foliage and fruit, as based on observations of 7 year old specimens grown near Modesto, Calif., with color in accordance with Munsell Book of Color.

Tree:

*Size.*—Large. Usually pruned to 3 to 3.5 meters in height and width for economical harvesting of fruit. Average spread 3 meters, varies with different types of soil and cultural practices.

*Vigor.*—Vigorous, growth of 1.5 to 2 meters in height the first growing season. Varies with type of soil, fertility, climatic conditions and cultural practices.

*Branching habit.*—Semi-spreading, usually pruned to vase shape. Crotch angle approximately 35°, increases with heavy crop load.

*Productivity.*—Productive, usually thinning and spacing of fruit necessary, fruit set varies with climatic conditions at bloom time.

*Bearer.*—Regular, 4 consecutive years of adequate fruit set, no alternate bearing observed.

*Fertility.*—Self sterile, pollinator required.

*Density.*—Medium dense. Pruned to vase shape to allow sunlight and air movement to center of tree to enhance health of fruit spurs.

*Hardiness.*—Tree grown in USDA Hardiness Zone 9. Hardy in all stone fruit growing areas of California. Winter chilling requirement approximately 550 to 600 hours at or below 45° F.

Trunk:

*Size.*—Medium stocky. Average circumference 50.8 cm at 25.4 cm above ground on a 7 year old tree.

*Stocky.*—Medium.

*Texture.*—Medium shaggy, increases with age of tree.

*Color.*—Varies from 10YR 2/2 to 2.5Y 6/2.

Branches:

*Size.*—Medium to large. Average circumference 22.8 cm at 1.2 meters above ground on a 7 year old tree.

*Surface texture.*—New growth relatively smooth. Mature growth medium rough.

*Lenticels.*—Average number 44 in a 25.8 square cm surface area of branch. Size — large. Average length 3.7 mm. Average width 2.3 mm. Color varies from 2.5Y 6/6 to 2.5Y 5/6.

*Color.*—New growth exposed to sun 2.5YR 4/4 to 2.5YR 3/4. New growth not exposed to sun 2.5GY 6/8 to 2.5GY 5/8. Mature growth 2.5Y 5/2 to 2.5Y 4/2, varies with age of growth.

Leaves:

*Size.*—Medium. Average length 87.8 mm. Average width 54.3 mm.

*Form.*—Elliptic.

*Apex.*—Cuspidate.

*Base.*—Obtuse.

*Margin.*—Serrulate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Size — medium. Average length 25.9 mm. Average width 1.4 mm. Color varies from 2.5GY 7/4 to 5GY 8/4, where exposed to the sun the color varies from 5R 4/6 to 5R 3/6. Shallow, longitudinal groove. Surface — glabrous.

*Glands.*—Type — globose. Size — medium to large. Average length 0.7 mm. Average diameter 0.6 mm. Average number 3, varies from 1 to 4. Located on upper portion of petiole and base of leaf blade. Color varies from 2.5GY 8/4 to 5GY 8/4.

*Color.*—Upper surface varies from 5GY 4/4 to 5GY 4/8. Lower surface varies from 2.5GY 5/4 to 5GY 5/4. Midrib color varies from 2.5GY 9/4 to 5GY 9/4.

*Venation.*—Pinnately veined.

Flower buds:

*Size.*—Small to medium. Average length 10.8 mm. Average diameter 5.8 mm.

*Hardiness.*—Hardy in all stone fruit growing areas of California.

*Form.*—Conical, becoming slightly elongated before opening.

*Pedicel.*—Average length 2.8 mm. Average width 0.8 mm. Color varies from 2.5GY 8/6 to 2.5GY 7/6.

*Color of buds.*—N 9.5/ (white). Apex occasionally will have shade of light pink during first expansion which fades to white.

*Number of buds per spur.*—Varies from 2 to 5. Average number 4.

Flowers:

*Size.*—Small to medium. Average height 10.1 mm. Average diameter 20.1 mm.

*Petals.*—Number — 5, alternately arranged to sepals. Size — medium. Average length 11.2 mm. Average width 9.2 mm. Form — obovate, narrows at point of attachment. Margin — sinuate. Both surfaces glabrous. Color N 9.5/ (white).

*Sepals.*—Number — 5, alternately arranged to petals. Size — small. Average length 3.7 mm. Average width 3.1 mm. Both upper and lower surfaces glabrous. Form — triangular, apex pointed. Color — upper surface varies from 10Y 7/6 to 10Y 6/8. Lower surface varies from 10RP 4/8 to 10R 4/12.

*Stamens.*—Average number per flower 28. Average filament length 7.4 mm. Filament color N 9.5/ (white). Anther color 7.5Y 8.5/8 to 5Y 8/8.

*Pollen.*—Self sterile, pollinator required. Abundant, pollen sacs full. Color 7.5Y 8/8.

*Pistil.*—Number — normally 1, varies from 1 to 2. Surface — pubescent. Average length 10.8 mm.

Position of stigma — average of 1.0 mm below anthers. Color varies from 2.5GY 8.5/4 to 2.5GY 8/4.

*Fragrance.*—Slight aroma.

*Blooming period.*—Date of 1st Bloom Feb. 15, 2005. Date of Petal Fall Feb. 25, 2005. Varies slightly with climatic conditions.

*Color.*—N 9.5/ (white).

*Number flowers per flower bud.*—Normally 1, varies from 1 to 2.

*Pedicel.*—Average length 3.3 mm. Average width 0.8 mm. Color varies from 2.5GY 8/8 to 2.5GY 7/8.

Fruit:

*Maturity when described.*—Firm ripe.

*Date of 1st picking.*—Jun. 13, 2005.

*Date of last picking.*—Jun. 18, 2005, varies slightly with climatic conditions.

*Size.*—Medium to large. Average diameter axially 56.7 mm. Average transversely in suture plane 59.3 mm. Average weight 139.2 grams, average weight varies slightly with fertility of the soil, amount of thinning and climatic conditions.

*Form.*—Globose.

*Suture.*—Very slightly lipped, extends from base to apex.

*Ventral surface.*—Very slightly lipped.

*Apex.*—Slightly retuse.

*Base.*—Flat to slightly retuse.

*Cavity.*—Rounded, to slightly elongated in suture plane. Average depth 6.1 mm. Average diameter 11.2 mm.

Stem:

*Size.*—Small. Average length 7.8 mm. Average diameter 2.1 mm.

*Color.*—Varies from 2.5GY 5/6 to 5GY 6/8.

Flesh:

*Ripens.*—Evenly.

*Texture.*—Firm, meaty.

*Fibers.*—Few, very small, tender.

*Firmness.*—Firm, much firmer than most commercial apricots, similar in firmness to most commercial plums.

*Aroma.*—Wanting.

*Amydgalin.*—Undetected.

*Eating quality.*—Good.

*Flavor.*—Good, with a good balance between sugar and acid.

*Juice.*—Moderate, enhances flavor.

*Brix.*—Average 14.4°, varies slightly with amount of fruit per tree and climatic conditions.

*Color.*—Varies from 10YR 7/10 to 10YR 7/12. Pit cavity non-bleeding, color varies from 5YR 5/10 to 7.5YR 6/10.

Skin:

*Thickness.*—Medium.

*Surface.*—Nearly smooth.

*Down.*—Moderate amount, very short.

*Tendency to crack.*—None.

*Color.*—Ground color varies from 2.5Y 8.5/10 to 2.5Y 8/8. Overspread with 2.5R 4/8 to 5R 3/10. In areas near apex very small areas of ground color is exposed to surface giving a speckling pattern.

*Tenacity.*—Tenacious to flesh.

*Astringency.*—None.

Stone:

*Type.*—Clingstone.

*Size.*—Large. Average length 28.0 mm. Average width 23.0 mm. Average thickness 13.5 mm.

*Form.*—Ovoid.

*Base.*—Usually flat, varies from flat to slightly rounded.

*Apex.*—Rounded.

*Surface.*—Slightly pitted throughout, a very shallow groove on each side of suture.

*Sides.*—Unequal, one side extends further from suture plane.

*Ridges.*—A very small, narrow ridge on each side of suture.

*Tendency to split.*—None.

*Color.*—Varies from 10YR 7/6 to 10YR 6/6 when dry.

Kernel:

*Form.*—Ovate.

*Viability.*—Viable, complete embryo development.

*Size.*—Medium. Average length 16.0 mm. Average width 11.6 mm. Average depth 6.4 mm.

*Skin color.*—Varies from 2.5Y 9/4 to 5Y 9/4 when dry.

Use: Dessert. Market — local and long distance.

Keeping quality: Good, held firm in storage 2 weeks at 38° to 42° F. without internal breakdown of flesh, shriveling or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

That which is claimed is:

1. A new and distinct interspecific tree, substantially as illustrated and described, characterized by its large size, vigorous, semi-spreading growth and being a regular and productive bearer of medium to large size fruit with good flavor and eating quality; the fruit is further characterized by having an attractive red skin color, firm flesh and being relatively uniform in size and maturity, in comparison to its maternal proprietary parent (38GH36) it has pubescent skin compared to smooth skin and is approximately 18 days earlier in maturity.

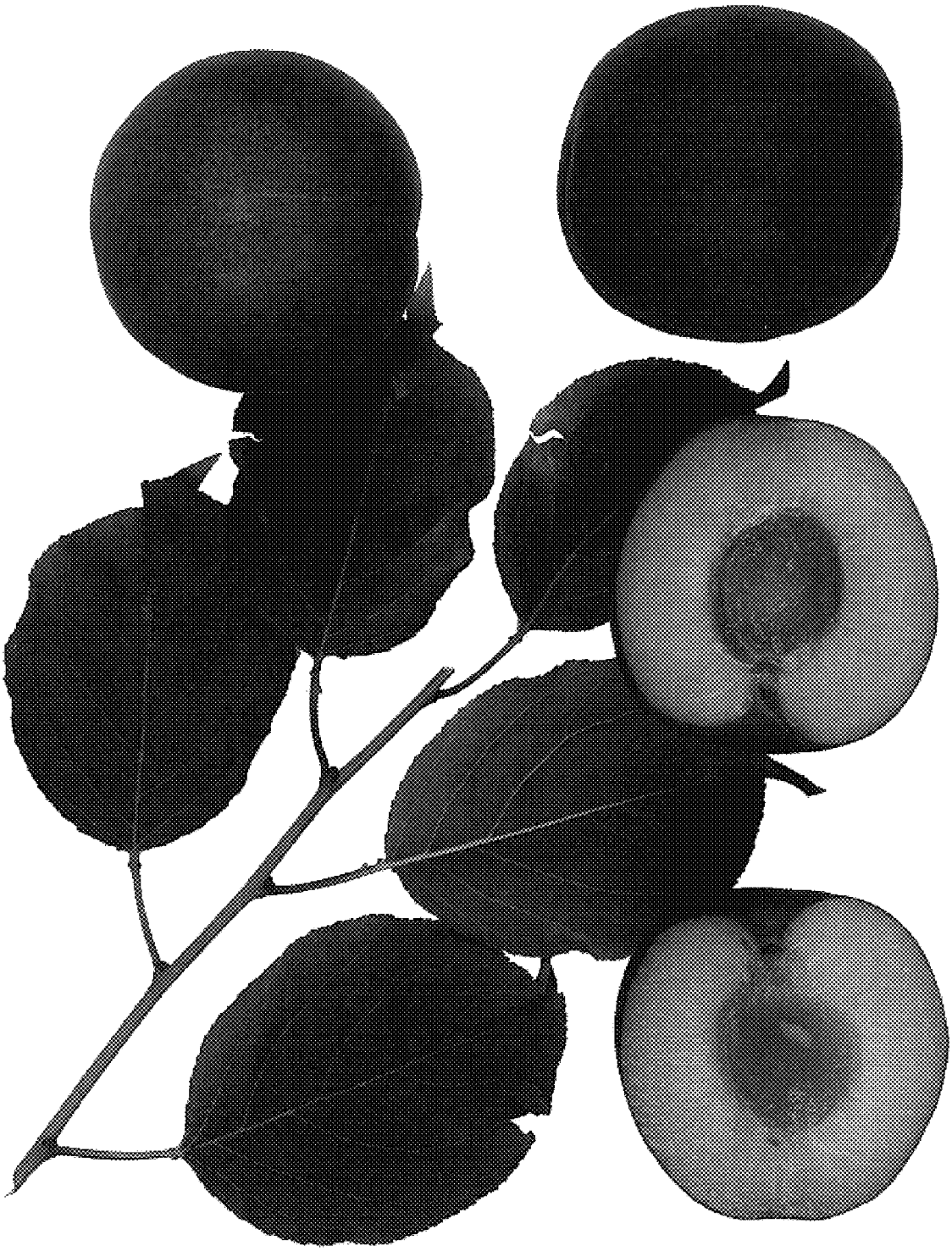

* * * * *